United States Patent
Neeley et al.

(10) Patent No.: US 10,088,389 B2
(45) Date of Patent: Oct. 2, 2018

(54) AUTOMATIC RECORDING AND GRAPHING OF MEASUREMENT DATA

(71) Applicant: Fluke Corporation, Everett, WA (US)

(72) Inventors: John Neeley, Seattle, WA (US); Bradey Honsinger, Everett, WA (US); Tyler Bennett Evans, Edmonds, WA (US); Joseph V. Ferrante, Redmond, WA (US)

(73) Assignee: Fluke Corporation, Everett, WA (US)

( * ) Notice: Subject to any disclaimer, the term of this patent is extended or adjusted under 35 U.S.C. 154(b) by 171 days.

(21) Appl. No.: 14/214,645

(22) Filed: Mar. 14, 2014

(65) Prior Publication Data

US 2014/0266765 A1   Sep. 18, 2014

Related U.S. Application Data

(60) Provisional application No. 61/876,719, filed on Sep. 11, 2013, provisional application No. 61/801,380, filed on Mar. 15, 2013.

(51) Int. Cl.
 *G01M 99/00* (2011.01)
 *G06F 15/00* (2006.01)
 (Continued)

(52) U.S. Cl.
 CPC ............. *G01M 99/00* (2013.01); *G01D 1/00* (2013.01); *G01D 7/00* (2013.01); *G01D 7/02* (2013.01);
 (Continued)

(58) Field of Classification Search
 CPC .. G01D 7/08; G01D 9/00; G01D 1/00; G01D 7/00; G01M 99/00; H04Q 2209/40;
 (Continued)

(56) References Cited

U.S. PATENT DOCUMENTS 5,386,117 A   1/1995 Piety
5,637,871 A   6/1997 Piety
(Continued)

FOREIGN PATENT DOCUMENTS

CA      2152024 A1   12/1995
CN    102852145 A    1/2013
(Continued)

OTHER PUBLICATIONS

Bicelli et al., "From the Traditional Multimeter to the "Wireless Multimeter Networking"," *IMTC 2006—Instrumentation and Measurement Technology Conference*, Sorrento, Italy, Apr. 24-27, 2006, pp. 1581-1586.
(Continued)

*Primary Examiner* — An T Nguyen
(74) *Attorney, Agent, or Firm* — Seed Intellectual Property Law Group LLP

(57) ABSTRACT

A method and system for capturing measurement data from a measurement device using a mobile computing device is provided. A mobile computing device is communicatively connected to one or more measurement devices, and receives measurement data from the one or more measurement devices. The mobile computing device stores the received measurement data. In some embodiments, the measurement devices have less storage space than the mobile computing device, and so the mobile computing device is capable of storing more measurements than the measurement devices are capable of storing. The mobile computing device is also capable of presenting the stored measurement data as a graph of a time series of values, which would not be possible using only the measurement device given its smaller memory.

21 Claims, 5 Drawing Sheets

(51) Int. Cl.

| | | |
|---|---|---|
| G08B 5/00 | (2006.01) | |
| G06T 11/20 | (2006.01) | |
| H04N 5/232 | (2006.01) | |
| H04N 5/33 | (2006.01) | |
| G01D 1/00 | (2006.01) | |
| G01D 7/00 | (2006.01) | |
| G06K 9/64 | (2006.01) | |
| G01D 9/00 | (2006.01) | |
| G06Q 20/08 | (2012.01) | |
| G08C 17/02 | (2006.01) | |
| H04Q 9/00 | (2006.01) | |
| G01D 7/08 | (2006.01) | |
| G01D 7/02 | (2006.01) | |
| G16H 10/40 | (2018.01) | |

(52) U.S. Cl.
CPC .............. *G01D 7/08* (2013.01); *G01D 9/00* (2013.01); *G06F 15/00* (2013.01); *G06K 9/64* (2013.01); *G06Q 20/085* (2013.01); *G06Q 20/0855* (2013.01); *G06T 11/206* (2013.01); *G08B 5/00* (2013.01); *G08C 17/02* (2013.01); *G16H 10/40* (2018.01); *H04N 5/23229* (2013.01); *H04N 5/33* (2013.01); *H04Q 9/00* (2013.01); *H04Q 2209/40* (2013.01); *H04Q 2209/47* (2013.01); *H04Q 2209/50* (2013.01); *H04Q 2209/86* (2013.01); *H04Q 2209/883* (2013.01)

(58) Field of Classification Search
CPC ........ H04Q 9/00; H04Q 2209/50; G08B 5/00; G06F 15/00; G06T 11/206; G08C 17/02; H04N 5/33; H04N 5/23229; G06Q 20/0855; G06Q 20/085; G06K 9/64
See application file for complete search history.

(56) References Cited

U.S. PATENT DOCUMENTS

| | | | |
|---|---|---|---|
| 5,664,207 | A | 9/1997 | Crumpler |
| 6,043,640 | A | 3/2000 | Lauby et al. |
| 6,601,111 | B1 | 7/2003 | Peacock et al. |
| 6,734,658 | B1 | 5/2004 | Bierer |
| 6,836,726 | B2 | 12/2004 | Sanchez Peiro |
| 7,076,239 | B2 | 7/2006 | Kirkup |
| 7,191,184 | B2 † | 3/2007 | Laborde |
| 7,304,618 | B2 | 12/2007 | Plathe |
| 7,454,050 | B2 | 11/2008 | Garvey |
| 7,478,305 | B2 | 1/2009 | Betawar |
| 7,528,372 | B2 | 5/2009 | Garvey, III |
| 7,552,029 | B2 | 6/2009 | Elwood et al. |
| 7,561,200 | B2 | 7/2009 | Garvey, III |
| 7,679,356 | B2 | 3/2010 | Garland et al. |
| 7,703,032 | B2 | 4/2010 | Wells |
| 7,706,596 | B2 | 4/2010 | Garvey |
| 7,728,275 | B2 | 6/2010 | Blanchard |
| 7,902,507 | B1 | 3/2011 | Garvey, III |
| 7,960,965 | B2 | 6/2011 | Lund |
| 7,995,830 | B2 | 8/2011 | Garvey |
| 8,003,942 | B2 | 8/2011 | Garvey, III |
| 8,119,986 | B1 | 2/2012 | Garvey, III |
| 8,124,923 | B2 | 2/2012 | Blanchard |
| 8,148,687 | B1 | 4/2012 | Praly |
| 8,300,922 | B1 | 10/2012 | Garvey, III |
| 8,334,513 | B1 | 12/2012 | Garvey, III |
| 8,358,903 | B1 | 1/2013 | Meads et al. |
| 8,368,001 | B2 | 2/2013 | Blanchard |
| 8,447,541 | B2 † | 5/2013 | Rada |
| 8,754,779 | B2 | 6/2014 | Ruther |
| 8,976,039 | B2 † | 3/2015 | O'Hara |
| 2001/0038343 | A1 | 11/2001 | Meyer |
| 2002/0059375 | A1 | 5/2002 | Pivowar et al. |
| 2002/0087266 | A1 | 7/2002 | Sugimoto et al. |
| 2002/0101374 | A1 | 8/2002 | Mutoh et al. |
| 2003/0058810 | A1 | 3/2003 | Petronic |
| 2003/0157895 | A1 | 8/2003 | Agrawal et al. |
| 2004/0244475 | A1 | 12/2004 | Butler et al. |
| 2004/0249605 | A1 | 12/2004 | Komatsu |
| 2005/0035966 | A1* | 2/2005 | Pasquarette ........... G06F 3/0486 345/440 |
| 2005/0125512 | A1 | 6/2005 | Fuller, III |
| 2006/0071812 | A1 | 4/2006 | Mason, Jr. |
| 2007/0118323 | A1 | 5/2007 | Ishizuka |
| 2007/0176933 | A1* | 8/2007 | Culpi ................... G06T 11/206 345/440.2 |
| 2007/0288206 | A1* | 12/2007 | Fujii ...................... G01D 1/00 702/189 |
| 2008/0231719 | A1 | 9/2008 | Benson |
| 2009/0128124 | A1 | 5/2009 | Garland et al. |
| 2009/0128125 | A1 | 5/2009 | Garland et al. |
| 2009/0128126 | A1 | 5/2009 | Garland et al. |
| 2009/0141593 | A1 | 6/2009 | Taha |
| 2010/0070273 | A1 | 3/2010 | Rodriguez et al. |
| 2010/0167659 | A1 | 7/2010 | Wagner |
| 2010/0181990 | A1 | 7/2010 | Hudson et al. |
| 2011/0099424 | A1 | 4/2011 | Rivera Trevino |
| 2011/0137678 | A1 | 6/2011 | Williams |
| 2011/0288810 | A1 | 11/2011 | Ishikawa |
| 2012/0001768 | A1 | 1/2012 | Radosavljevic et al. |
| 2012/0004886 | A1 | 1/2012 | Jordil |
| 2012/0030547 | A1 | 2/2012 | Raptis et al. |
| 2012/0047424 | A1 | 2/2012 | Rothschild |
| 2012/0079504 | A1 | 3/2012 | Maciocci et al. |
| 2012/0130223 | A1 | 5/2012 | Reicher |
| 2012/0154172 | A1* | 6/2012 | O'Hara ................... H04Q 9/00 340/870.02 |
| 2012/0172023 | A1 | 7/2012 | Griff |
| 2012/0178438 | A1 | 7/2012 | Vashi |
| 2012/0224067 | A1 | 9/2012 | Stuart |
| 2012/0229270 | A1 | 9/2012 | Morley |
| 2012/0270505 | A1 | 10/2012 | Prakash |
| 2012/0300089 | A1 | 11/2012 | Sbaiz |
| 2012/0320189 | A1 | 12/2012 | Stuart |
| 2013/0009788 | A1 | 1/2013 | Langenberg |
| 2013/0024783 | A1 | 1/2013 | Brakensiek et al. |
| 2013/0029683 | A1 | 1/2013 | Kim |
| 2013/0065633 | A1 | 3/2013 | Sridhara |
| 2013/0066576 | A1 | 3/2013 | Cs |
| 2013/0109375 | A1* | 5/2013 | Zeiler ................... H04W 4/028 455/426.1 |
| 2013/0124136 | A1 | 5/2013 | Neeley |
| 2013/0127904 | A1 | 5/2013 | Dove et al. |
| 2013/0307992 | A1 | 11/2013 | Erlandsson |
| 2014/0039838 | A1 | 2/2014 | Katz et al. |
| 2014/0149064 | A1* | 5/2014 | Davidson .............. G06F 15/00 702/130 |
| 2014/0278255 | A1 | 9/2014 | Anderson |
| 2014/0279443 | A1 | 9/2014 | Neeley et al. |
| 2015/0022181 | A1 | 1/2015 | Anderson et al. |

FOREIGN PATENT DOCUMENTS

| | | |
|---|---|---|
| EP | 2 026 079 A2 | 2/2009 |
| JP | 5-79585 A | 3/1993 |
| JP | 2004-245819 A | 9/2004 |
| JP | 2006-11642 A | 1/2006 |
| JP | 2006-309373 A | 11/2006 |
| JP | 2010-191540 A | 9/2010 |
| JP | 2010-286382 A | 12/2010 |
| JP | 2014-119585 A | 6/2014 |
| KR | 10-2008-0112692 A | 12/2006 |
| KR | 10-2012-0065540 A | 6/2012 |
| KR | 10-2012-0077332 A | 7/2012 |
| WO | 03/088830 A1 | 10/2003 |
| WO | 2010/076384 A8 | 7/2010 |

(56) References Cited

FOREIGN PATENT DOCUMENTS

| WO | 2013/020110 A2 | 2/2013 |
|---|---|---|
| WO | 2013/020110 A3 | 2/2013 |

OTHER PUBLICATIONS

Extended European Search Report, dated Nov. 24, 2014, for European Application No. 14175986.0-1954, 10 pages.
Extech Instruments, "Extech EX540 Wireless Datalogging selected as 2010 EC&M Product of the Year Category Winner," Press Release, Mar. 18, 2009, 2 pages.
Extech Instruments, "Extech EX845 METERLiNK™ Clamp Meter Transmit Readings to FLIR IR Cameras," Press Release, Apr. 1, 2010, 3 pages.
Extech Instruments, "MultiMeter/Datalogger with Wireless PC Interface," Product Datasheet, Jul. 14, 2011, 1 page.
Extech Instruments, "Wireless TRMS Multimeter—Model EX540," User's Guide, Apr. 1, 2010, 17 pages.
Fluke, "Fluke CNX™ Wireless Systems," Technical Data, 2013, 11 pages.
Microchip, "Auto-Ranging Analog-to-Digital Converter with 3-1/2 Digit Display," TC818A, 2005, 24 pages.
Oregon Scientific, "Full Wireless Weather Station," 2013, 2 pages.
Oregon Scientific, "Wireless Full Weather Station Kit," Model: WMR80 / WMR 80A, User Manual, 2008, 13 pages.
International Search Report and Written Opinion dated Sep. 12, 2014, in International Patent Application No. PCT/US2014/029867, filed Mar. 14, 2014, 12 pages.
International Search Report dated Jul. 10, 2014, in International Patent Application No. PCT/US2014/029561, filed Mar. 14, 2014, 2 pages.
International Search Report and Written Opinion dated Jul. 17, 2014, in International Patent Application No. PCT/US2014/029889, 13 pages.
International Search Report and Written Opinion dated Jul. 18, 2014, in International Patent Application No. PCT/US2014/029885, 16 pages.
International Search Report and Written Opinion dated Jul. 22, 2014, in International Patent Application No. PCT/US2014/029883, 13 pages.
International Search Report and Written Opinion dated Jul. 24, 2014, in International Patent Application No. PCT/US2014/029879, 12 pages.
Communication pursuant to Article 94(3) EPC, dated Jun. 27, 2016, for European Application No. 14 175 986.0-1954, 7 pages.
Revolution Wi-Fi, "Wake on Wireless LAN," Nov. 8, 2010, retrieved from http://revolutionwifi.blogspot.de/2010/11/wake-on-wireless-lan.html, retrieved on Jun. 17, 2016, 5 pages.
Wikipedia, "Wake-on-LAN," retrieved from https://en.wikipedia.org/w/index.php?fitle=Wake-on-LAN&oldid=558487738, retrieved on Jun. 17, 2016, 9 pages.
Extended European Search Report, dated Oct. 21, 2016, for European Application No. 14765607.8-1855 / 2973486, 10 pages.
Extended European Search Report, dated Nov. 25, 2016, for European Application No. 14764851.3-1568 / 2973071, 8 pages.
CN 201480027483.2 Office Action dated Feb. 1, 2018, 16 pages.
Japanese Notification of Rejection for JP Application No. 2016-503238 dated Apr. 10, 2018, with English Translation.
Extech Instruments press release titled Extech EX845 METERLiNK Clamp Meter Transmit Readings to FLIR IR Cameras, published on Apr. 1, 2010, 3 pages.†
Extech Instruments product datasheet titled MultiMeter/Datalogger with Wireless PC Interface, published on Jul. 14, 2011, 1 page.†
Extech Instruments press release titled Extech EX540 Wireless Datalogging DMM selected as 2010 EC&M Product of the Year Category Winner, published on Mar. 19, 2010, 2 pages.†
Extech Instruments user manual titled Wireless TRMS Multimeter Model EX540 published Mar. 2011, 17 pages.†
Extech Instruments user manual titled "Wireless TRMS Multimeter Model EX540" published Mar. 2011.†
Extech Instruments press release titled "Extech EX540 Wireless Datalogging DMM selected as 2010 EC&M Product of the Year Category Winner" published on Mar. 19, 2010.†
Extech Instruments product datasheet titled "MultiMeter/Datalogger with Wireless PC Interface" published on Jul. 14, 2011.†
Extech Instruments press release titled "Extech EX845 METERLiNK Clamp Meter Transmit Readings to FLIR IR Cameras" published on Apr. 1, 2010.†

\* cited by examiner
† cited by third party

AUTOMATIC RECORDING AND GRAPHING OF MEASUREMENT DATA

CROSS-REFERENCE TO RELATED APPLICATIONS

This application claims the benefit of U.S. Provisional Application No. 61/801,380, filed Mar. 15, 2013, and U.S. Provisional Application No. 61/876,719, filed Sep. 11, 2013, the disclosures of which are incorporated by reference herein in their entirety.

BACKGROUND

Measurement tools such as digital multimeter (DMM) devices, heat-sensing infrared cameras, vibration meters, and the like are used in a wide array of industrial, commercial, and residential settings to measure a variety of properties of equipment. In production facilities, plants, and factories, for example, it is critical to ensure that equipment remains operational. Interruptions in production for unexpected failure of equipment can be costly. Such facilities typically establish procedures for routine monitoring and maintenance of equipment that include using measurement tools.

For example, a technician using a handheld measurement tool may be tasked to periodically measure a property of equipment to assess the functional "health" of the equipment or to determine the presence of a fault. To perform such measurements, the technician travels to the site of the equipment, manually records data from the measurement tool, and returns to a central location to produce a report. Unfortunately, the technician may need to return multiple times to the site of the equipment to obtain the desired data. Further, analysis of measured data obtained from the equipment often requires the technician to manually enter the measured data into a computer.

In some instances, an equipment maintenance process includes obtaining readings of measurement data from multiple measurement tools at different locations, and sometimes includes obtaining measurements simultaneously or in close time proximity. Furthermore, complex calculations may be desired to be quickly performed on measured data obtained at the different locations, even when using measurement tools with limited or no functionality for storing or processing measurements over time. What is desired are systems and methods that allow guidance and coordination to be provided with respect to collecting measurements using measurement tools, and that allow measurement data to be efficiently collected and processed.

SUMMARY

The following summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a system for collecting measurement data from a device under test (DUT) is provided. The system comprises a measurement device and a mobile computing device. The measurement device comprises at least one sensor. The mobile computing device comprises at least one processor, a measurement collection engine configured to obtain measurements from the at least one sensor of the measurement device; a measurement data store configured to store a plurality of measurements obtained by the measurement collection engine; and a nontransitory computer-readable medium. The nontransitory computer-readable medium has computer-executable instructions stored thereon that, in response to execution by the at least one processor, cause the mobile computing device to receive a time series of measurements of the DUT from the measurement device; store the time series of measurements in the measurement data store; and present a graph of the time series of measurements to a user. The measurement data store of the mobile computing device includes storage space for concurrently storing more measurement data than can be concurrently stored by the measurement device.

In some embodiments, a method for collecting measurement data from a device under test (DUT) is provided. A mobile computing device receives a time series of measurements of the DUT from a measurement device. The mobile computing device stores the time series of measurements in a measurement data store accessible by the mobile computing device, and presents a graph of the time series of measurements to a user. The measurement data store accessible by the mobile computing device includes storage space for concurrently storing more measurement data than can be concurrently stored by the measurement device.

In some embodiments, a computer-readable medium having computer-executable instructions stored thereon is provided. The computer-executable instructions, in response to execution by one or more processors of a mobile computing device, cause the mobile computing device to collect measurement data from a device under test (DUT) by receiving a time series of measurements of the DUT from a measurement device; store the time series of measurements in a measurement data store accessible by the mobile computing device; and present a graph of the time series of measurements to a user. The measurement data store accessible by the mobile computing device includes storage space for concurrently storing more measurement data than can be concurrently stored by the measurement device.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

In various embodiments, disclosed herein are systems and methods for capturing, storing, analyzing, and reporting data obtained from measurement devices, such as handheld measurement tools and other sensors that perform measurements of equipment. Such systems and methods are useful, in part, for improving the speed, accuracy, and ease of use of measurement data collected from measurement devices, especially where the measurement data results from multiple simultaneous or near simultaneous measurements of different types of data.

As will be better understood from the following description, the term "measurement data" refers to data that is generated by a measurement device and directly or indirectly relates to or reflects a measured property of a device under test. In various embodiments, measurement devices may measure many types of properties, such as electrical and/or mechanical properties. Properties that may be measured by measurement devices include, for example and without limitation, electrical current, voltage, resistance, capacitance, inductance, vibration, humidity, pressure, light, time, temperature, sound, material composition, and the like.

Figure 1:
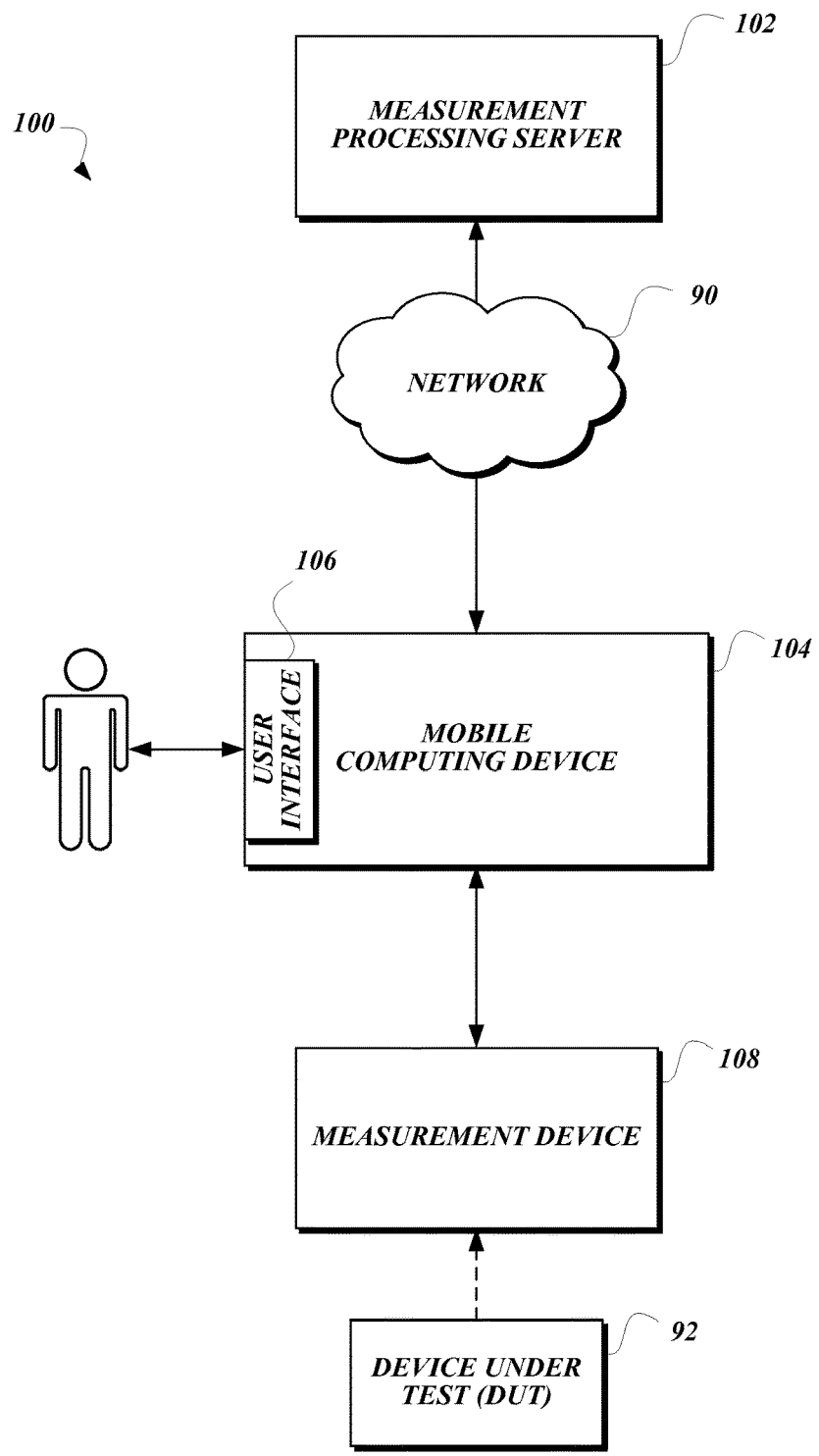
FIG. 1 is a schematic diagram that illustrates, at a high level, an exemplary embodiment of a system according to various aspects of the present disclosure.

FIG. 1 is a schematic diagram that illustrates, at a high level, an exemplary embodiment of a system according to various aspects of the present disclosure. In the illustrated embodiment, the system 100 includes a mobile computing device 104. The mobile computing device 104 is configured to interact with at least one measurement device 108 positioned with respect to equipment to be measured, such as the illustrated device under test (DUT) 92.

In some embodiments, the mobile computing device 104 may be a general purpose mobile computing device, such as a smart phone that provides cellular telephony, cellular data, Bluetooth, Wi-Fi, and/or other types of wireless connectivity, which is further programmed to provide functions as described herein. An application (or "app") executing on the mobile computing device 104 may provide processes for data collection, storage, analysis, and communication as described herein. A user interface 106 is presented by the mobile computing device 104, which allows a user to view data that is collected and analyzed by the computing device 104, and to control the collection, processing, storage, and transmission thereof as discussed further below.

In various embodiments, the measurement device 108 may be, for example, a measurement tool such as a DMM, a Wi-Fi network tester, a vibration tester, an infrared or thermal imaging camera, and/or the like that is capable of measuring a property of a DUT 92 and providing measurement data based thereon. Generally, measurement devices 108 may be handheld or portable, and may include any type of testing or sensing device or multipurpose device capable of performing a measurement or a combination of types of measurements. Measurement devices 108 may also include single purpose or multi-purpose sensors that are capable of measuring properties of equipment.

In various embodiments, data communication between measurement devices 108 and the mobile computing device 104 may be wireless or wired, and may use any type of standardized or proprietary communication protocol. Current standardized protocols for wired communication include, for example, USB, Firewire, Ethernet, and the like, while wireless data communication may be performed using ZigBee, Bluetooth, Wi-Fi, cellular data transmission protocols, and the like. The communication may be a direct communication between the measurement device 108 and the mobile computing device 104, or may take place over a network with one or more intervening network devices providing a communication path. In some embodiments, at least some of the processing described herein as being performed by the mobile computing device 104 could be performed by the measurement processing server 102. In such embodiments, the measurement device 108 may be configurable to communicate directly with the measurement processing server 102 via a wireless or wired communication path, and may use any type of standardized or proprietary communication protocol, including but not limited to the illustrated network 90.

In an environment where multiple measurement devices 108 are used to measure different properties of equipment, the mobile computing device 104 may be configured to choose measurement devices 108 with which to communicatively interact to receive measurement data, as well as analyze, display, and further communicate the measurement data to one or more locations remote from the equipment and/or the mobile computing device 104.

In at least one implementation, a user may establish communication links between the mobile computing device 104 and one or more measurement devices 108 that are positioned with respect to one or more DUTs 92. As each communication link is established, measurement data generated by the respective measurement devices 108 may automatically be communicated to the mobile computing device 104. When measurement data is no longer received from a measurement device 108, e.g., the measurement device 108 drops out of range of the mobile computing device 104, the mobile computing device 104 discontinues or releases the communication link. As will be discussed in greater detail below, measurement data previously received from the measurement device 108 may be stored by the mobile computing device 104 in association with the measurement device 108 and/or the test point (or points) being measured on the equipment, but upon discontinuing or releasing the communication link, the mobile computing device 104 no longer displays live data measurements from the measurement device 108 nor indicates an active communication link with the measurement device 108.

When the user no longer desires to receive measurement data from a particular measurement device 108, the user may cause the mobile computing device 104 to disconnect or release the communication link with the measurement device 108. Subsequently, the measurement device 108 may return to a low power operational mode in which the measurement device 108 periodically communicates a presence detect signal, as previously described. If desired, the measurement device 108 may be configured to locally store measurement data in a data store present on the measurement device 108, which later may be read by a mobile computing device 104 upon establishing a new communication link with the measurement device 108.

In some wireless environments, the mobile computing device 104 may be paired with a measurement device 108 in order to receive measurement data from the measurement device 108. Pairing adds a layer of security over such communication between the measurement device 108 and the mobile computing device 104 in that establishing a communication link with the measurement device 108 may utilize additional data that is typically accessible only to persons or devices authorized to engage in such communication.

As measurement data is received, the mobile computing device 104 may display the measurement data to the user via the user interface 106. In some embodiments, the displayed measurement data represents instantaneous measurements received from the measurement devices 108. When storage of the measurement data is desired, the user may initiate collection of the measurement data, such as by pressing a "Capture" or "Record" button on the user interface 106. For example, in at least one implementation, pressing a "Capture" button on the user interface 106 may cause the mobile computing device 104 to save a single set of the measurement data obtained at an instance of time. On the other hand, by pressing a "Record" button, the user may initiate a recording of multiple sets of the measurement data in which the mobile computing device 104 saves a time series of the measurement data received from the measurement device 108. If desired, such recordings may be presented to the user as a data graph or an image video on the display of the mobile computing device 104.

In some embodiments, the data obtained by the mobile computing device 104 may further include status or safety information regarding the measurement device 108 (as opposed to the DUT 92). For instance, if the status of the measurement device 108 justifies display of a warning light on the measurement device 108, information regarding that status may be transmitted to the mobile computing device 104 and a corresponding icon may be displayed on the mobile computing device 104 noting the condition of the measurement device 108. Some nonlimiting examples of a status that would justify the display of a warning light include a low battery status, an out-of-range indicator, a lead indicator, and the like. This may be particularly helpful to a user whose mobile computing device 104 is connected to multiple measurement devices 108. Such icon display helps the user to recognize when one or more of the measurement devices 108 need attention to ensure that correct measurement data is being obtained.

In some embodiments, data may also be conveyed between a measurement device 108 and the mobile computing device 104 using techniques other than via a communication protocol as described above. As a nonlimiting example, in some embodiments, data may be exchanged between the measurement device 108 and the mobile computing device 104 through transfer of physical media, such as a memory card that is transferred between memory slots in the measurement device 108 and the mobile computing device 104. As another nonlimiting example, in some embodiments, data may be displayed by the measurement device 108 in a human-readable format (such as via an analog instrument meter with analog display, or via a LCD or other indicator that presents a digital value) and the mobile computing device 104 may obtain the measurement data by capturing and processing an image of the measurement device 108. In yet another nonlimiting example, in some embodiments, data may be displayed by the measurement device 108, and a user may manually enter the data into the mobile computing device 104 via the user interface 106.

While in some embodiments, the mobile computing device 104 is the device in the system 100 responsible for obtaining, processing, and storing measurement data from measurement devices 108, in other embodiments, the mobile computing device 104 may also or instead communicate the measurement data to one or more measurement processing servers 102, which may be located at one or more local or remote locations. Such communication may be performed through a network 90 such as a wired or wireless network, and may involve local, wide area, or global data communication links, such as the Internet. In some embodiments, such communication may be performed by syncing the mobile computing device 104 to another computing device (such as a desktop computing device, a laptop computing device, a tablet computing device, and/or the like) via a dock, a physical communication cable, a wireless communication technology, or a network, and the other computing device may then act as the measurement processing server 102. In some embodiments, the other computing device may receive the data from the mobile computing device 104 and then subsequently transmit the data to the measurement processing server 102 via the network 90. In some embodiments, the mobile computing device 104 may obtain, process, and store the measurement data locally while unable to access the network 90, such as when there is no access to a cellular data network due to a lack of wireless signal strength at a measurement location. The mobile computing device 104 may then transmit the measurement data to one or more measurement processing servers 102 as discussed above upon being reconnected to a network 90 or otherwise communicatively coupled to another computing device.

Figure 2:
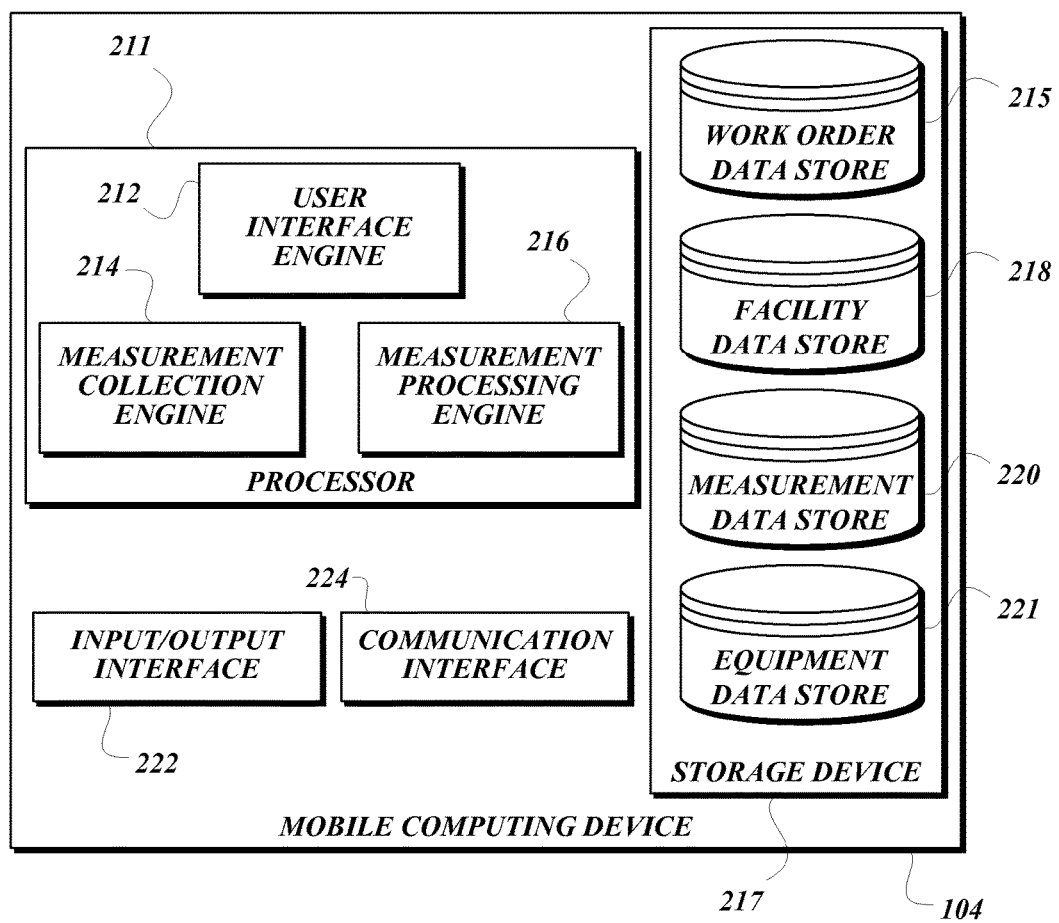
FIG. 2 is a block diagram that illustrates an exemplary mobile computing device according to various aspects of the present disclosure.

FIG. 2 is a block diagram that illustrates an exemplary mobile computing device 104 according to various aspects of the present disclosure. As illustrated, the mobile computing device 104 may include a processor 211, at least one communication interface 224, at least one data storage device 217, and at least one input/output (I/O) interface 222, among other elements. As used herein, the term processor is not limited to integrated circuitry, otherwise referred to as a computer, but broadly refers to a microcontroller, a microcomputer, a microprocessor, a programmable logic controller, an application specific integrated circuit, other programmable circuits, combinations of the above, and/or the like. The processor 211 generally serves as a computational center of the mobile computing device 104 by supporting the execution of instructions that cause the device to receive, store, analyze, and communicate data using the communication interface 224, the storage device 217, and/or the input/output interface 222.

The communication interface 224 may include one or more components configured to communicate with external devices, such as another mobile computing device, a computer system at a remote location, a measurement device 108, and/or the like. All such communication may be wired or wireless. In some embodiments, the mobile computing device 104 may process measurement data into different forms and communicate the processed measurement data to such external devices. In some embodiments, the measurement data is organized and stored by the mobile computing device 104 in the storage device 217. The stored measurement data may later be retrieved, analyzed, and communicated.

The storage device 217 may comprise any form of computer-readable storage media, such as any currently available or later developed media suitable for storing computer-executable instructions and data that are accessible to one or more device components, such as the processor 211. Computer-readable storage media may be removable or nonremovable and may be volatile or nonvolatile. Examples of computer-readable storage media may include hard drives as well as RAM, ROM, EEPROM, flash types of memory, and/or the like.

The input/output interface 222 may include one or more input devices such as dials, switches, or buttons, and one or more output devices, such as a display or printer. Generally, the input/output interface 222 allows a user or an external system to interact with programs being executed by the mobile computing device 104. In at least one embodiment, the input/output interface 222 allows a user to control or configure the mobile computing device 104 to receive data from a measurement device 108 and to analyze, store, and/or communicate the measurement data to an external device. Information regarding the configuration of measurement devices and the equipment properties that they measure may be stored in the storage device 217 and used by the processor 212 when interacting with the measurement devices 108.

As an output device, a display may include, without limitation, a liquid crystal display (LCD), a light emitting diode (LED) device, an organic light emitting diode (OLED) device, and/or the like. The display may be capable of displaying color images, though embodiments disclosed herein also work with black and white displays. The display may include a touch screen that, in some embodiments, incorporates aspects of an input device into the display. The touch screen may be any type of touch screen currently known or later developed. For example, the touch screen may be a capacitive, infrared, resistive, or surface acoustic wave (SAW) device. In response to input received by the input device, the mobile computing device 104 may receive, analyze, store, and communicate data related to measurement of properties of equipment. In some measurement applications, the touch screen may be suitable for use in industrial settings, for example, where the touch screen is configured to receive inputs through gloved hands.

In addition to a touch screen or other display, the input/output interface 222 of the mobile computing device 104 may further include one or more input devices that communicate an input to the mobile computing device 104. As mentioned earlier, such input device may include, as examples, buttons, switches, trigger switches, selectors, rotary switches, or other input devices known to those of ordinary skill in the art. In at least one embodiment, measurement devices may be configured to perform measurements in response to user input or user selection of an input that is provided to the mobile computing device 104 via the one or more input devices.

As illustrated, the processor 211 may be configured to provide one or more engines. In general, the term "engine," as used herein, refers to logic embodied in hardware or software instructions, which can be written in a programming language, such as C, C++, COBOL, JAVA™, PHP, Perl, HTML, CSS, JavaScript, VBScript, ASPX, Objective C, Ruby, Microsoft .NET™ languages such as C#, and/or the like. An engine may be compiled into executable programs or written in interpreted programming languages. Software engines or applications may be callable from other engines or from themselves. Generally, the engines described herein refer to logical modules that can be merged with other engines or applications, or can be divided into sub-engines. The engines can be stored in any type of computer-readable medium or computer storage device, such as the storage device 217, and be stored on and executed by one or more general purpose processors (such as processor 211), thus creating a special purpose computing device configured to provide the engine. In some embodiments, the engines described herein may be incorporated into one or more applications or "apps" installed on the mobile computing device 104. The illustrated engines may be provided by the processor 211 in response to execution by the processor of computer-executable instructions stored on a computer-readable medium, such as the storage device 217.

As illustrated, the engines provided by the processor 211 may include a user interface engine 212, a measurement collection engine 214, and a measurement processing engine 216. The measurement collection engine 214 is configured to interact with one or more measurement devices 108 via the communication interface 224. The measurement collection engine 214 may instruct the measurement devices 108 to obtain measurement data, and may receive measurement data from the measurement devices 108. The measurement collection engine 214 may also store the received measurement data in the measurement data store 220. Additionally, the measurement collection engine 214 may receive warning status information from the measurement devices 108, and may cause the user interface engine 212 to present corresponding icons and/or notifications. The measurement processing engine 216 may perform processing over measurements stored in the measurement data store 220, or may process measurements obtained by the measurement collection engine 214 before storage in the measurement data store 220. For example, the measurement processing engine 216 may group measurements with other related measurements, may assign metadata to a received measurement, and/or perform other processing on the measurements as described elsewhere herein. As will be described below, the metadata includes group identifying information that associates the stored measurement data with other data annotated with similar group identifying information.

The user interface engine 212 is configured to generate a user interface for presentation to a user via the input/output interface 222 of the mobile computing device 104. The user interface generated by the user interface engine 212 may allow the user to configure the measurement collection engine 214 to communicate with various measurement devices 108, and may allow the user to configure the measurement devices 108 to capture measurements per the user's input. The user interface generated by the user interface engine 212 may allow the user to instruct the measurement collection engine 214 to store a given measurement or a time series of measurements, may allow the user to observe currently obtained measurements, and may allow the user to browse and/or compare previously collected and stored measurements.

In some embodiments, the interface provided by the user interface engine 212 may also provide guidance to the user for assisting in collecting measurements. For example, in some embodiments, the user interface engine 212 may be configured to present a task list to the user representing a set of measurements to be obtained. In some embodiments, the user interface engine 212 may be configured to present a map to the user in order to guide the user to a location at which measurements are to be obtained, to assist the user in identifying equipment from which measurements have been obtained, and/or to assist the user in locating test points to be monitored on the equipment.

As illustrated, the storage device 217 may include a work order data store 215, a facility data store 218, a measurement data store 220, and an equipment data store 221. The measurement data store 220 may be configured to store measurements received by the mobile computing device 104, and also may be configured to store metadata associated with said measurements. The facility data store 218 may be configured to store information about a facility, such as floor plans, equipment locations, identifiers of installed equipment, test points on the equipment, and/or the like. The equipment data store 221 may be configured to store information about equipment that has been monitored (or is intended to be monitored in the future) using the system 100. For example, in some embodiments, the equipment data store 221 may store information associated with units of equipment such as location information, model information, make information, equipment identifiers, photos, and test points. The work order data store 215 may be configured to store work order information that helps guide a user through a series of measurements to be completed. In some embodiments, the work order data store 215 may also be configured to store progress information along with a given work order to indicate which tasks within the work order have been completed and which are yet to be performed.

As understood by one of ordinary skill in the art, a "data store" as described herein may be any suitable device, or a data structure on a computer-readable medium, configured to store data for access by a computing device. One example of a data store is data stored in an organized manner on a storage medium such as storage device 217. Another example of a data store (which may be more relevant to the data stores provided by the measurement processing server 102 described further below) is a highly reliable, high-speed relational database management system (DBMS) executing on one or more computing devices and accessible over a high-speed packet switched network. Yet another example of a data store is a non-relational network-based storage system, such as the Amazon S3 store provided by Amazon.com, Inc., Google Cloud Storage provided by Google, Inc., a distributed hash table (DHT), and/or the like. However, any other suitable storage technique and/or device capable of quickly and reliably providing the stored data in response to queries may be used to provide a data store, and the computing device may be accessible locally instead of over a network, or may be accessible over some other type of suitable network or provided as a cloud-based service. For example, though the data stores in FIG. 2 are illustrated as being present on the storage device 217 of the mobile computing device 104, in some embodiments, the data stores may not be resident on the mobile computing device 104 but may instead be remotely accessible by the mobile computing device 104. One of ordinary skill in the art will recognize that separate data stores described herein may be combined into a single data store, and/or a single data store described herein may be separated into multiple data stores, without departing from the scope of the present disclosure.

Figure 3:
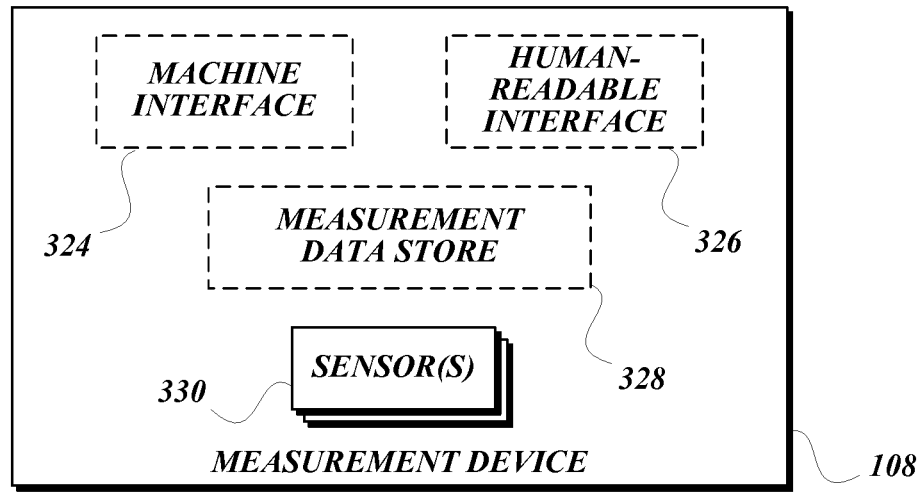
FIG. 3 is a block diagram that illustrates an exemplary embodiment of a measurement device according to various aspects of the present disclosure.

FIG. 3 is a block diagram that illustrates an exemplary embodiment of a measurement device according to various aspects of the present disclosure. As illustrated, the measurement device 108 includes one or more sensors 330, and optionally includes a machine interface 324, a human-readable interface 326, and a measurement data store 328.

The sensors 330 are devices associated with the measurement device 108 that collect information regarding properties of a device under test, and convert the information to a useable form. For example, a voltage sensor may sense a voltage across two test leads applied to the device under test, and may output a value indicating the sensed voltage for use by other components of the measurement device 108. Likewise, a temperature sensor may detect a temperature of a portion of the device under test, and may output a value indicating the temperature. In some embodiments, the sensors 330 may be integrated into a single case along with the rest of the components of the measurement device 108. In some embodiments, one or more of the sensors 330 may be located external from a case containing other components of the measurement device 108, and may communicate to the measurement device 108 using any suitable technique.

In some embodiments, the measurement device 108 may include one or more sensors 330 that are placed on or near test points of the equipment to be measured. Such sensors 330 may be temporarily affixed to the equipment or to structures near the equipment. Alternatively or in addition, the sensors 330 may be incorporated into test devices that a user can relocate from one test point to another on the equipment as needed.

In some embodiments, the measurement device 108 may be a handheld measurement tool. A handheld measurement tool is generally configured to be held in a user's hand while measuring a property of equipment. However, it should be appreciated that a handheld measurement tool need not always be held in a user's hand and may be positioned by a user away from the user's hand, for example, by affixing or hanging the tool from a support or placing the tool on or near a test point on the equipment to be measured. In some embodiments, the measurement device 108 is a device other than a handheld measurement tool. For example, the measurement device 108 may be, for example, a portable measurement tool that is not necessarily intended to be used while held in the hand. While not permanently connected to the equipment being measured, such portable tools are useful for measuring properties of the equipment over days or weeks, as desired.

In some instances, the measurement device 108 may log measurements of equipment properties over time, and may store the measurements in the measurement data store 328. Later, the mobile computing device 104 may obtain the measurements stored in the measurement data store 328. In some embodiments, the stored measurements may be obtained by the mobile computing device 104 via the machine interface 324, if the machine interface 324 is available, or via the human-readable interface 326, if the human-readable interface 326 is available and provides access to the stored measurements.

In some embodiments, the measurement data store 328 may be omitted. In such embodiments, the mobile computing device 104 may collect measurements from the sensors 330 via the machine interface 324 or the human-readable interface 326 as they are obtained by the sensors 330. The mobile computing device 104 may then provide storage functionality by storing the measurements in the measurement data store 220, thus allowing historical measurements to be collected, analyzed, and presented even when the measurement device 108 does not itself include a measurement data store 328. When desired, the mobile computing device 104 may display one or more graphs showing the measurement data as received over time, even from the measurement devices 108 that do not include the measurement data store 328.

The machine interface 324 may be any suitable machine-readable interface, such as a wireless communication interface or a wired communication interface as discussed above. In some embodiments, the machine interface 324 may be used to obtain measurements from the sensors 330 in real time or substantially in real time as measurements are obtained by the sensors 330, with or without the measurements being stored in the measurement data store 328. In some instances, the measurement device 108 may also include a human-readable interface 326. The human-readable interface 326 may display values obtained by the sensors 330 to the user in real time or substantially real time, and may provide access to stored past measurements in the measurement data store 328. The human-readable interface 326 may include a video display, a LCD display, an analog display, an indicator light, or any other suitable display. In some embodiments, similar information may be obtained via the machine interface 324 and the human-readable interface 326, while in some embodiments, different information may be obtained via the two interfaces.

Figure 4:
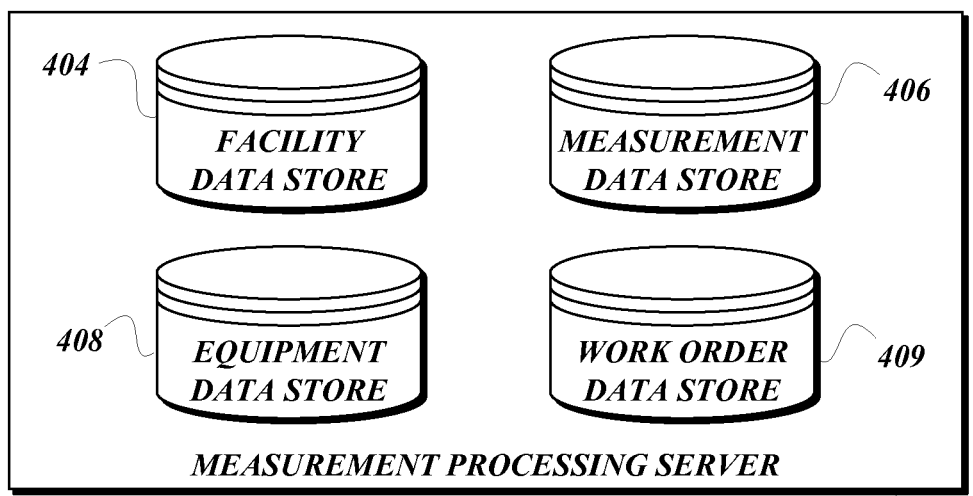
FIG. 4 is a block diagram that illustrates an exemplary embodiment of a measurement processing server according to various aspects of the present disclosure.

FIG. 4 is a block diagram that illustrates an exemplary embodiment of a measurement processing server 102 according to various aspects of the present disclosure. As illustrated, the measurement processing server 102 may be configured to provide a facility data store 404, a measurement data store 406, an equipment data store 408, and a work order data store 409. The facility data store 404, the measurement data store 406, and the work order data store 409 may be configured to store information similar to that stored by the facility data store 218, the measurement data store 220, and the work order data store 215, respectively, discussed above with respect to FIG. 2. However, in some embodiments, the data stores present on the measurement processing server 102 may receive and store data collected by more than one mobile computing device 104, or provided by multiple management computing devices for distribution to mobile computing devices 104. This may be useful for many purposes, including but not limited to comparing measurements taken of similar equipment at different locations and different times, centralized distribution of task lists and equipment information, and the like.

The equipment data store 408 may be configured to store information about equipment of particular makes, models, and/or the like. For example, for a given piece of equipment, the equipment data store 408 may store maintenance guidelines, user manuals, standard specifications, normal operating parameters, testing instructions, and/or the like. This information may be provided to a mobile computing device 104 to assist in performing measurements. The facility data store 404 may include unique identifiers used to identify particular installations of equipment at a facility, and may refer to information stored in the equipment data store 408 to provide further description of the equipment.

One of ordinary skill in the art will recognize that the illustration of components as being present on the measurement processing server 102 is exemplary only, and that in some embodiments, components of measurement processing server 102 may instead be located on the mobile computing device 104, or split between the measurement processing server 102 and the mobile computing device 104.

Figure 5:
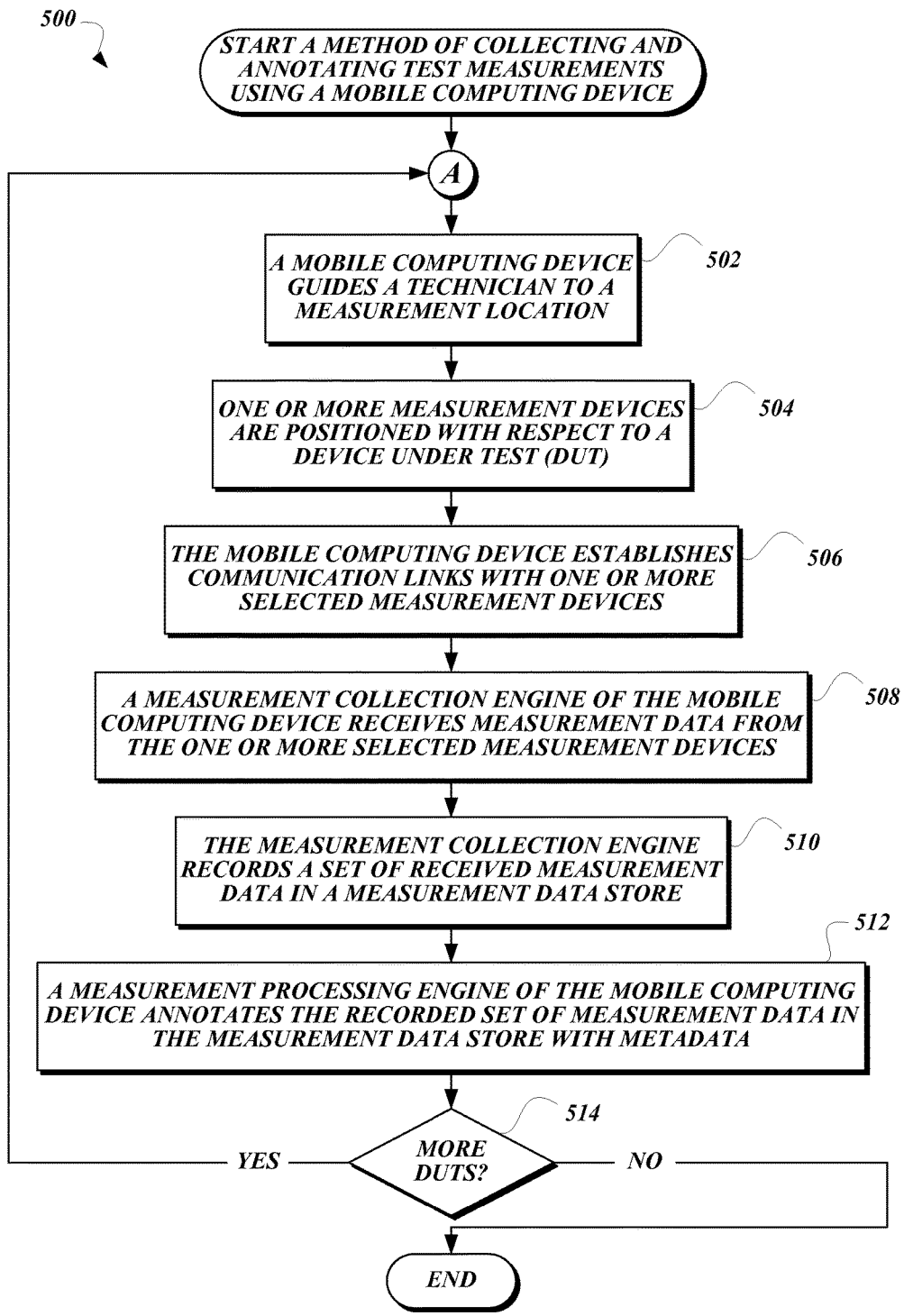
FIG. 5 is a flowchart that illustrates an exemplary embodiment of a method of collecting and annotating test measurements using a mobile computing device according to various aspects of the present disclosure.

FIG. 5 is a flowchart that illustrates an exemplary embodiment of a method 500 of collecting and annotating test measurements using a mobile computing device 104, according to various aspects of the present disclosure. From a start block, the method 500 proceeds to a continuation terminal ("terminal A"), and from terminal A to block 502, where a mobile computing device 104 guides a technician to a measurement location. Generally, a measurement location is a location at which a mobile computing device 104 can communicate with a measurement device 108 configured to measure properties of a device under test. In some embodiments, the measurement location may be in close proximity to the device under test, such that a handheld or other portable measurement device 108 may be placed in contact with the device under test or otherwise obtain measurement data from the device under test. In some embodiments, the measurement location may be in proximity to a network via which the mobile computing device 104 may communicate with a measurement device 108 configured to measure properties of a device under test at a different location. In some embodiments, the mobile computing device 104 may guide the technician to the measurement location by presenting a map, floor plan, or travel directions to the technician. In some embodiments, it may be assumed that the technician knows the location of the device under test, and the mobile computing device 104 may guide the technician to the measurement location by presenting a task list and an indication of the device to be tested.

Next, at block 504, one or more measurement devices 108 are positioned with respect to a device under test (DUT) 92, as illustrated in FIG. 1. For example, a sensor of the measurement device 108 may be placed in physical or electrical contact with the DUT 92 to detect a property such as vibration, voltage, resistance, and/or the like. As another example, a sensor of the measurement device 108 capable of sensing properties without being in physical contact with the DUT 92, such as a clamp meter, an infrared camera, and/or the like, may be positioned to sense a property of the DUT 92. One of ordinary skill in the art will recognize that, in some embodiments, the actions described in blocks 502 and 504 may be swapped in order, such as in embodiments where the measurement devices are left in position for monitoring the DUT 92 even between collections of measurements using a mobile computing device 104.

At block 506, the mobile computing device 104 establishes communication links with one or more selected measurement devices 108. The communication links may include transmission of data via a communication protocol or by any other technique discussed above or otherwise known to one of ordinary skill in the art. In some cases, the measurement devices 108 may initially operate in a mode in which the measurement devices 108 periodically communicate a signal indicating their presence, which the mobile computing device 104 can detect. The user may be required to initiate an input, such as press a button, on the measurement devices 108 or otherwise cause the measurement devices 108 to commence communicating such a presence detect signal. In any event, upon detection of the presence of one or more measurement devices 108, the mobile computing device 104 may display the availability of the measurement devices 108 to the user via the user interface 106.

The user may indicate to the mobile computing device 104 the particular measurement device 108 or devices that should be linked to the mobile computing device 104 for communication of measurement data. For example, in at least one implementation, the user may press particular buttons on the mobile computing device 104 that are associated with the available measurement devices 108. As another example, the user may touch particular text or icons on the user interface 106 presented on a touchscreen of the mobile computing device 104 to indicate a desire to link the mobile computing device 104 with the measurement devices 108. In response to such user indication, the mobile computing device 104 establishes communication links with the indicated measurement devices 108, e.g., by responding to the presence detect signal that is periodically sent by the measurement devices 108. The measurement devices 108 and the mobile computing device 104 may exchange configuration information that allows for exclusive or nonexclusive communication of measurement data from the measurement devices 108. In yet other embodiments, the mobile computing device 104 may automatically establish communication links with all measurement devices 108 that it detects.

Next, at block 508, a measurement collection engine 214 of the mobile computing device 104 receives measurement data from the one or more selected measurement devices 108. In some embodiments, the measurement data may be received via a network or wireless protocol of the communication link. In some embodiments, the measurement data may be received via other means. As nonlimiting examples, in some embodiments, the measurement data may be received by exchanging a tangible computer-readable medium between the mobile computing device 104 and a measurement device 108, by manual entry of the measurement data into the mobile computing device 104 by the technician, by capturing an image of the measurement device 108 using a camera of the mobile computing device 104, and/or using any other suitable technique. The measurement data may include a single value representing a property of the DUT 92 at a given time, or may include multiple values representing a time series of values representing a property of the DUT 92 over a period of time. At block 510, the measurement collection engine 214 records a set of received measurement data in a measurement data store 220. The set of received measurement data may include a single reading from a single sensor 330, multiple readings from a single sensor 330, or one or more readings from multiple sensors 330.

The method 500 then proceeds to block 512, where a measurement processing engine 216 of the mobile computing device 104 annotates the recorded set of measurement data in the measurement data store 220 with metadata. In some embodiments, the metadata used to annotate the recorded set of measurement data may include information describing when, where, and how the information was collected including, but not limited to: a timestamp; a GPS location (or a location obtained using other positioning technology) of the mobile computing device 104 and/or the measurement device 108; an equipment identifier that either uniquely identifies the DUT 92 or identifies a type or model of the DUT 92; an identifier of the measurement device 108; a record of settings of the measurement device 108; the particular test point or points on the DUT 92; a work order, task list, or job instruction that directed the collection of the measurement data; an identity of the technician collecting the measurement data; a text note; a voice note; an image; a video; an image annotation; and/or the like. In some instances, the DUT 92 may be labeled with human perceptible data, such as on a sticker, hang tag, or the like, that identifies the particular equipment. The technician may enter the equipment identity into the mobile computing device 104 based on the labeled data. In other instances, the DUT 92 may be labeled with a machine readable code, such as a barcode, a QR code, or a radio frequency identification (RFID) tag, that the technician can scan using the mobile computing device 104. Alternatively or in addition, the equipment identity and other information may be provided by a barcode or QR code printed on a work order delivered to the technician conducting the equipment measurements. The equipment identity corresponding to the scanned code can then be automatically stored in the metadata of the measurement data that is automatically being associated in a particular data group.

In some embodiments, the metadata used to annotate the recorded set of measurement data may include group identifying information. The group identifying information may associate the recorded set of measurement data with other recorded sets of measurement data, and this association may then be used to display or otherwise process the grouped sets measurement data together. In some embodiments, the group identifying information may include one or more group identifiers that may be automatically associated with the recorded set of measurement data. In at least one implementation, the mobile computing device 104 may associate measurement data into a group based on an element that is common to the metadata of each received data measurement, such as time information that reflects when the data was measured. For example, measurement data that is captured simultaneously or near in time to each other, such as within a predetermined amount of time of each other, from various measurement devices 108 may automatically be grouped into a single data group, and the data group may be associated with a particular test point or group of test points of the DUT 92. The identity of the test point or group of test points may be supplied by the user, either before, during, or after receipt of the measurement data. In other implementations, the identity of the test point or group of test points may automatically be obtained from the DUT 92, from the measurement devices 108, or from the mobile computing device 104 or other devices. For example, a GPS circuit in a measurement device 108 may provide location data that can be included with or otherwise associated with the measurement data being transmitted to the mobile computing device 104. In some cases, the location data may be associated in a memory or other storage device with one or more test points. The location data may be used (e.g., as an index or keyword for look up in a table) to identify particular test points associated with the location, either in the measurement devices 108 or in the mobile computing device 104.

For example, multiple sets of measurement data taken with different measurement devices 108 of the same DUT 92 (such as visual images, infrared images, and/or thermal images captured by a camera or thermal imager, electrical measurements such as voltage, current, or impedance measurements captured by a DMM, and measurement of mechanical parameters such as vibration or pressure captured by portable sensors, and/or the like) obtained at substantially the same time (such as, for example, within a few seconds or minutes of each other) may be grouped together to be displayed and/or analyzed as part of a single test. Said grouping may also be based on group identifying information specified by the technician or on some other piece of common metadata other than the timestamp. For example, measurement data captured within a predetermined distance of each other as determined by a positioning system may be grouped together.

As another example, sets of measurement data taken of different DUTs 92 that are the same type of equipment (such as, for example, two different units of the same model of a motor) may be grouped together to provide comparisons between multiple separate units. The mobile computing device 104 may also be configured to receive text, capture an image, or record audio or video initiated by the technician, such as a voice comment or text annotation of measurement data or as a recording of equipment appearance or sound, and associate such text, image, or audio/video recordings with the measurement data in a particular group. As yet another example, a technician may provide commentary on observations of the DUT 92 at the time the measurement data is obtained. Such commentary may be received from the technician before, during, or after the data measurements occur. By saving the user-initiated text or audio/video recordings with metadata that is held in common with the measurement data, the text or audio/video recordings may likewise be associated in the same group with the measurement data.

A feature of the present disclosure is that group identifying information may be generated either before, during, or after the measurement data is obtained. In instances where measurement data is captured before the group identifying information is generated, the measurement data may automatically be associated in a group according to parameters such as the time or location when the data is measured or transmitted.

Automatically generated groups may be presented to the technician with a prompt for the technician to confirm the automatically generated information or to supply further group identifying information. The technician can input information pertaining to the group and have the information stored in the metadata. For example, the technician may enter information regarding the measured equipment and have the identity of the equipment stored with the measurement data in the group. In some embodiments, the technician manually inputs the identity of the measured equipment. In other embodiments, the mobile computing device 104 may display a list of previously identified equipment and allow the technician to select the equipment being measured. If the equipment being measured is not included in the displayed list, the technician may initiate a prompt on the mobile computing device 104 that allows the technician to create a new equipment identity and store the equipment identity in the list for later retrieval when the equipment is again being measured. In yet other embodiments, the mobile computing device 104 may receive or sense location data (e.g., through a GPS reading or other positioning technology) and automatically provide a list of known equipment associated with the location data, from which the technician can select the equipment record matching the DUT 92. In still other embodiments, the mobile computing device 104 may automatically generate a group based on work order data, either by grouping all measurements gathered while processing a work order, by obtaining equipment identifiers using the work order data, and/or using any other suitable technique.

Next, the method 500 proceeds to a decision block 514, where a determination is made regarding whether more devices remain to be tested. If the result of the determination at decision block 514 is YES, the method 500 proceeds to terminal A, and the actions discussed with respect to blocks 502 through 514 are repeated for the next device to be tested. Otherwise, if the result of the determination at decision block 514 is NO, the method 500 proceeds to an end block and terminates.

In various embodiments, data groups that have been generated by the mobile computing device 104 may be presented to the user in a variety of formats for viewing, analyzing, and reporting. For example, a textual description of a data group or a visual graph of measurement data in the data group may be shown to the user. In instances where a data group includes a large amount of measurement data, the user may be presented with a small portion or short description of the measurement data with a prompt that the user may select to receive additional detail regarding the data measurements in the group. If desired, the user may divide the measurement data in a data group into two or more smaller data groups. Information that distinguishes the two or more smaller groups is stored in the metadata of the data measurements pertaining to the smaller groups.

By automatically associating data into data groups, an improved process is provided for easily organizing and presenting the measurement data to the user in a clear, straightforward, and visual manner. The measurement data is packaged and/or formatted in a way that makes it easy for the user and others to analyze the data in the different data groups and evaluate the status of the equipment being measured.

In some embodiments, the system 100 disclosed herein may be particularly useful for large organizations that have a desire to monitor or otherwise measure a large number of units of equipment, or to monitor or otherwise measure a large number of properties of a given unit of equipment. Accordingly, some embodiments of the present disclosure further provide a unified data collection and reporting interface for equipment being measured. These embodiments include processes for collecting data from disparate measurement devices positioned to obtain measurements of equipment in one or more locations, storing the measurement data in one or more associated data structures, and reporting the measurement data in a unified display.

One example of a unified display is a single, scrollable "equipment page" presented by the user interface engine 212 that is associated with particular equipment and provides a view of the measurement data captured and/or processed with regard to the equipment. By storing and displaying disparate data collected with regard to a given unit or type of equipment on a single page, a user is able to evaluate both historical data and presently measured data, observe trends in the data, determine the status of the equipment, and predict future maintenance needs of the equipment. Such analysis may be conducted by a technician on site with the equipment or by management personnel and/or experts at remote locations that have access to the unified data collection and reporting interface for the equipment.

In some cases, it may be helpful to a user to compare the measurement data of particular equipment to the measurement data of similar equipment in other locations, particularly if the health status of the other equipment has already been established. Equipment pages for installations of similar equipment may be displayed in a manner (e.g., side-by-side or picture-in-picture) that facilitates comparison of the measurement data obtained from a DUT 92 to overall trends shown in other installations of similar equipment. Comparing the DUT 92 with similar equipment in other locations may facilitate evaluation of a health status of the DUT 92.

Figure 6:
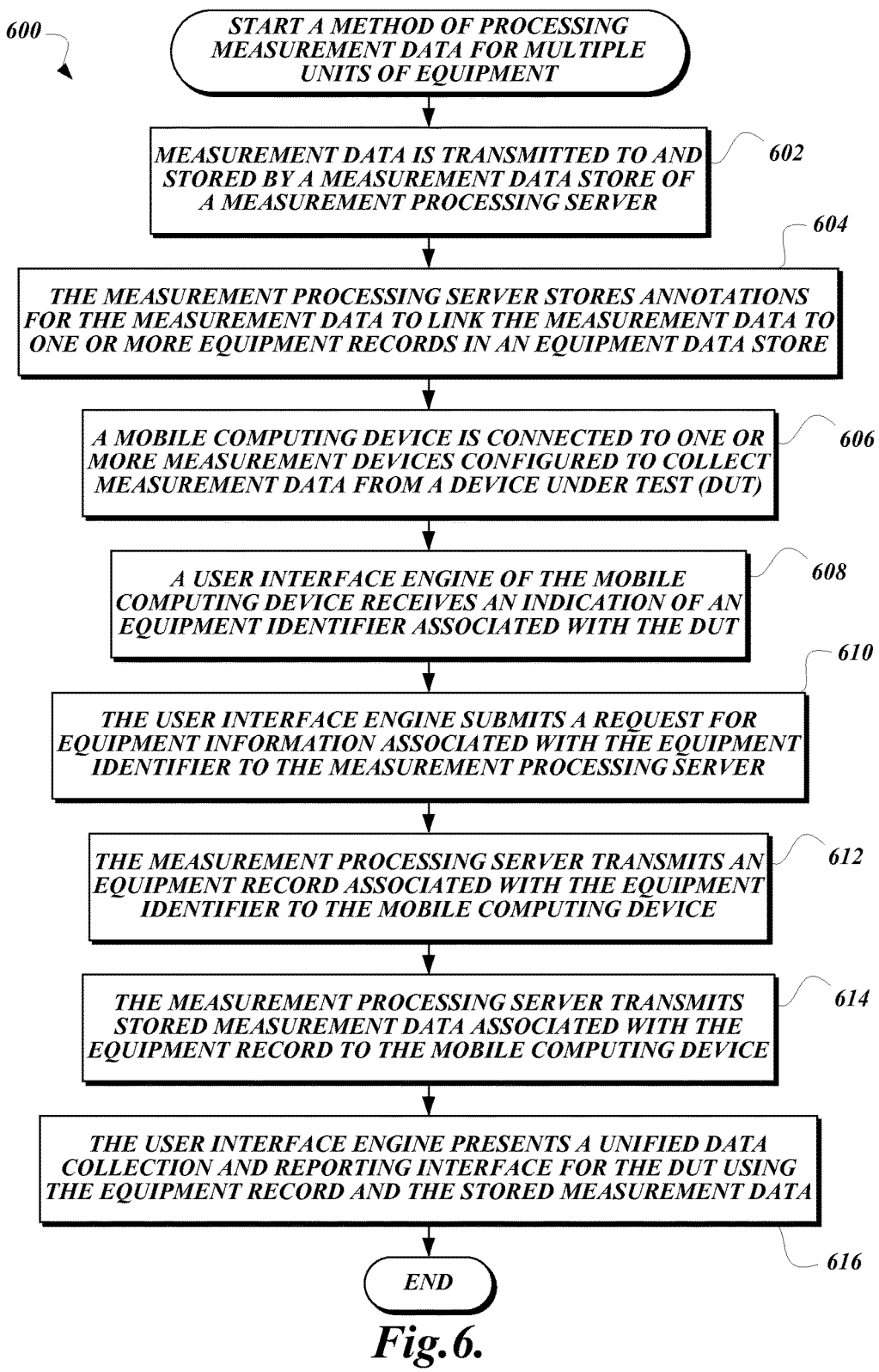
FIG. 6 is a flowchart that illustrates an exemplary method of processing measurement data for multiple units of equip-

FIG. 6 is a flowchart that illustrates an exemplary method 600 of processing measurement data for multiple units of equipment to generate a unified data collection and reporting interface according to various aspects of the present disclosure. From a start block, the method 600 proceeds to block 602, where measurement data is transmitted to and stored by a measurement data store 406 of a measurement processing server 102. The measurement data stored in block 602 represents measurements collected from one or more units of equipment. In some embodiments, the measurement data may have been collected using a method similar to the method illustrated in FIG. 5 and discussed above, though in other embodiments, any other suitable method may be used to obtain the measurement data. Next, at block 604, the measurement processing server 102 stores annotations for the measurement data to link the measurement data to one or more equipment records in an equipment data store 408. In some embodiments, the annotation that links the measurement data to one or more equipment records may be an equipment identifier that uniquely identifies an equipment record in the equipment data store 408, and may be added along with the rest of the metadata stored with the measurement data. One of ordinary skill in the art may consider the actions described above in blocks 602-604 as providing the system 100 with historical measurement data for use in creating the unified data collection and reporting interface as described below.

Once the system 100 has obtained some historical measurement data for equipment to be compared to the DUT 92, a unified data collection and reporting interface may be generated by the system 100. Accordingly, the method 600 proceeds to block 606, where a mobile computing device 104 is connected to one or more measurement devices 108 configured to collect measurement data from one or more DUT 92, as described above. Next, at block 608, a user interface engine 212 of the mobile computing device 104 receives an indication of an equipment identifier associated with the DUT 92. The equipment identifier may be provided in a human-perceptible form on a name plate, hang tag, sticker, label, and/or the like attached to the DUT 92. In some embodiments, the equipment identifier may be entered into the mobile computing device 104 by manual entry, by scanning of text on the DUT 92, by scanning a bar code or QR code label, and/or by any other suitable technique, similar to the techniques discussed above. Meanwhile, in other embodiments, the equipment identifier may be determined by the technician selecting equipment matching the DUT 92 from the unified data collection and reporting interface presented by the user interface engine 212.

Production plants, factories, facilities, etc., typically have multiple installations of equipment of a given type at different locations. The unified data collection and reporting interfaces for different equipment installations may be organized in the mobile device and in remote data processing centers to enable a technician to quickly identify and select particular equipment for viewing of the corresponding interface. In various embodiments, attributes such as equipment name, type, location, and status may be used to distinguish different installations of equipment. The unified data collection and reporting interfaces for the different equipment installations may include such equipment attributes. The equipment attributes may be displayed to facilitate user identification and selection of a desired installation of equipment.

For example, the location of equipment may be identified by a textual description of the equipment's surroundings. Alternatively or in addition, graphical depictions illustrating the location of the equipment relative to its surroundings may be provided. For example, a map showing a floor plan of a factory or facility having multiple equipment installations may be shown with icons representing particular equipment installations within the factory or facility. The icons may be positioned within an image of the floor plan to illustrate the respective locations of the equipment. In instances where the map is larger than the available area on the display, the depiction of the map may be scrollable in one or more dimensions to enable easy access to the complete floor plan map.

In some embodiments, the map may be a formal illustration of a floor plan. In other embodiments, the map may be a hand drawn sketch generated by a technician and saved in the unified data collection and reporting interface for the equipment. The image of the floor plan may be, for example, a photograph of a sketch or formal illustration on paper, or it may be a sketch drawn directly onto the screen of the display. Images of the equipment stored in the unified data collection and reporting interface for the equipment may further facilitate identification of the particular equipment. Depicting a floor plan map or other graphical image of equipment surroundings may help a technician to physically find particular equipment. Accordingly, a technician sent to measure data with regard to particular equipment may be guided when attempting to locate the equipment on site.

In some embodiments, the map data may include GPS or other positioning information. In such embodiments, a mobile computing device 104 capable of receiving or generating GPS data may superimpose an icon onto a depiction of the map indicating the position of the mobile computing device 104 relative to equipment and other surroundings in the map. Such depictions may further guide a technician sent to measure data with regard to particular equipment.

A technician may also use map data to identify particular equipment that the technician is seeking to evaluate. For example, in at least one embodiment, a graphical map may be displayed to the technician showing various equipment installations. The technician can then touch or click a mapped location on the display to select particular equipment at that location. Selection of the particular equipment causes the equipment identifier for that equipment to be selected.

Alternatively or in addition to graphically depicting a map showing equipment installations, a mobile computing device 104 may display a listing of building areas or room types (potentially organized in a hierarchy) that enables a technician to identify and select particular equipment for evaluation. An exemplary embodiment may provide a list of building areas, such as basement, floor, wall, or roof, that are associated with the locations of different equipment. Upon selection of a building area, the mobile computing device 104 may further display a more detailed list of rooms or locations within the selected building area. Upon selection of a room or location within the building area, the technician may then be provided a listing of equipment in the selected room or location. Eventually, the technician is able to identify and select particular equipment based on its relative location in the building, and thereby select the equipment identifier to be used.

Another exemplary embodiment may provide a listing of room types, such as boiler room, machine room, assembly floor, laboratory, office, and/or the like, where equipment is located. Upon selection of a room type, the mobile computing device 104 may further display a more detailed list of rooms that match the selected room type. Thereafter, upon selection of a particular room, the technician may be provided a listing of equipment in the selected room. The technician may then identify and select particular equipment from the list. Selection of particular equipment from the list causes the equipment identifier for that equipment to be used. In some embodiments, the map information, the locations of equipment, and/or the like may be stored in the facility data store 404 and obtained therefrom by the mobile computing device 104.

Once the equipment identifier is obtained, the method 600 proceeds to block 610, where the user interface engine 212 submits a request for equipment information associated with the equipment identifier to the measurement processing server 102. At block 612, the measurement processing server 102 transmits an equipment record associated with the equipment identifier to the mobile computing device 104.

At block 614, the measurement processing server 102 transmits stored measurement data associated with the equipment record to the mobile computing device 104. Once the mobile computing device 104 has received the stored measurement data and/or the equipment record, the method 600 proceeds to block 616, where the user interface engine 212 presents a unified data collection and reporting interface for the DUT 92 using the equipment record and the stored measurement data.

In various embodiments, the unified data collection and reporting interface for particular equipment may be configured to present reference documents stored in the equipment record that are helpful to the technician and others. For example, the equipment record may hold safety manuals or maintenance guidelines that the technician and others can access while operating the equipment, making measurements, or evaluating measurement data. In addition, work orders pertaining to the equipment and subsequent reports may be stored in the equipment record for later access.

In various embodiments, the unified data collection and reporting interface for particular equipment may also be configured to present the stored measurement data, either by itself or side-by-side with a current measurement value. For example, the interface may present a graph that shows trends in a measurement value over time for a given DUT 92, or for all similar measurement values collected from equipment of the same equipment type, and may also present the current measurement value for comparison. In various embodiments, the interface for particular equipment may also include features such as a status bar that quickly illustrates the current status of the equipment. For example, a green status bar may indicate equipment in good maintenance condition, while a yellow or red status bar may indicate equipment needing further attention. The status may be updated by a technician, or may be automatically determined by comparing a current measurement value or values to the stored measurement data or to acceptable values stored in the equipment record. The interface may include images of the equipment taken before, during, or after measurement data is obtained. Images of the equipment obtained over time may be compared to identify changes indicative of future maintenance needs. If desired, a tool may be provided in which a previously obtained image of the equipment is superimposed on an image to be taken or presented side-by-side with an image to be taken, allowing the technician to align the two images, which facilitates later comparison of the images. In some embodiments, the tool may also provide the ability to compare two previously obtained images for comparison to each other, either in a side-by-side presentation or superimposed on one another. In some embodiments, the tool may provide the ability to provide a side-by-side or superimposed comparison of images of different units of equipment. The interface may include collections of measurement data organized into groups as described above. A technician viewing the equipment page for particular equipment may select one or more of the data groups for further viewing and analysis.

When providing measurement data for viewing and analysis, the unified data collection and reporting interface may automatically provide graphs of the measurement data collected over time. Alternatively or in addition, data captured at a particular instance of time may be displayed as a static numerical value. Image data stored in the measurement data store 406 or equipment data store 408 may be displayed as images in the interface. Such images may be shown along with graphs and/or static numerical values of other measurement data to enable a broader, holistic view of the equipment. As will be understood by one of ordinary skill in the art, when image data is discussed herein, said image data may include visible light image data, infrared image data, or any other suitable type of image data.

Once the user has finished interacting with the unified data collection and reporting interface, the method 600 proceeds to an end block and terminates.

In some embodiments, the system 100 may be configurable to automatically generate reports in formats other than the unified data collection and reporting interface as well. For example, in some embodiments the mobile computing device 104, the measurement processing server 102 or some other computing device associated with the system 100 may include a report definition. The report definition may include measurements to be reported in a particular format, such as a regulatory form and/or the like. Upon collection of measurements to be entered in the form, the system 100 may automatically generate a report in the format indicated in the report definition, and may provide the report for submission to a regulatory agency, for storage in a record associated with the DUT, and/or the like.

While embodiments of systems and methods have been illustrated and described in the foregoing description, it will be appreciated that various changes can be made therein without departing from the spirit and scope of the present disclosure. For example, while embodiments of the mobile computing device have been described in the context of a smart phone executing one or more programmed applications, other embodiments of the mobile computing device may include a handheld measurement tool that is additionally capable of measuring properties of equipment. The measurement devices, as indicated earlier, may include handheld measurement tools as well as multipurpose and single use sensors that are positioned relative to equipment to be measured. Computer-executable instructions that cause one or more computing devices to perform processes as described herein may be stored in a nontransitory computer readable medium accessible to the one or more computing devices. Moreover, it should be understood that rearrangement of structure or steps in the devices or processes described herein that yield similar results are considered within the scope of the present disclosure. Accordingly, the scope of the present disclosure is not constrained by the precise forms that are illustrated for purposes of exemplifying embodiments of the disclosed subject matter.

The embodiments of the invention in which an exclusive property or privilege is claimed are defined as follows:

1. A system for evaluating measurement data of an installation of a device under test (DUT) with measurement data of an installation of equipment that is different than the DUT but of a same equipment type as the DUT, the system comprising:
    a mobile computing device comprising:
        at least one processor;
        a measurement collection engine configured to obtain measurements from multiple measurement devices, wherein at least one measurement device measures a first parameter of the DUT at a first time, and wherein at least one other measurement device measures a second parameter of an installation of other equipment of the same equipment type as the DUT at a second time that is different than the first time;
        a measurement data store configured to store a plurality of measurements obtained by the measurement collection engine; and
        a nontransitory computer-readable medium having computer-executable instructions stored thereon that, in response to execution by the at least one processor, cause the mobile computing device to:
            receive a first time series of measurements of the DUT and a second time series of measurements of the other equipment of the same equipment type as the DUT, wherein the first time series of measurements includes measurements of the first parameter obtained by the at least one measurement device at the first time, and the second time series of measurements includes measurements of the second parameter obtained by the at least one other measurement device at the second time;
            store the first and second time series of measurements in the measurement data store; and
            present a graph of the first and second time series of measurements to a user,
    wherein the instructions cause the mobile computing device to retrieve measurement data and concurrently present the measurement data in the graph showing a comparison of measurement data obtained over time from measurement of the DUT and from measurement of the other equipment of the same equipment type as the DUT.

2. The system of claim 1, wherein the measurement device does not have a measurement data store for storing measurement data.

3. The system of claim 1, wherein the instructions further cause the mobile computing device to present a current measurement as a numeric value side-by-side with the graph of the first and second time series of measurements.

4. The system of claim 1, wherein the at least one measurement device includes more than one sensor, and wherein the instructions further cause the mobile computing device to present separate graphs of values retrieved from each sensor of the at least one measurement device.

5. The system of claim 1, wherein the at least one measurement device is configured to provide a warning status based on measurements obtained by the measurement device,
wherein the measurement collection engine of the mobile computing device is further configured to receive a warning status provided by the measurement device, and
wherein the instructions further cause the mobile computing device to display an icon to a user corresponding to the warning status provided by the measurement device and received by the measurement collection engine.

6. The system of claim 1, wherein the measurement data store is further configured to store metadata associated with one or more stored measurements.

7. The system of claim 6, wherein the metadata includes one or more of a name, a location, and operational parameters.

8. A method for evaluating measurement data of an installation of a device under test (DUT) with measurement data of an installation of equipment that is different than the DUT but of a same equipment type as the DUT, the method comprising:
receiving, by a mobile computing device, a first time series of measurements of a first parameter of the DUT obtained by a first measurement device at a first time;
receiving, by the mobile computing device, a second time series of measurements of a second parameter of an installation of other equipment of the same equipment type as the DUT obtained by a second measurement device at a second time that is different than the first time;
storing, by the mobile computing device, the first and second time series of measurements in a measurement data store accessible by the mobile computing device; and
presenting a graph of the first and second time series of measurements to a user,
wherein presenting the graph of the first and second time series of measurements to a user includes retrieving measurement data and concurrently presenting the measurement data in the graph showing a comparison of measurement data obtained over time from measurement of the DUT and from measurement of the other equipment of the same equipment type as the DUT.

9. The method of claim 8, wherein the measurement device does not have a measurement data store for storing measurement data.

10. The method of claim 8, further comprising presenting a current measurement as a numeric value side-by-side with the graph of the first and second time series of measurements.

11. The method of claim 8, further comprising presenting separate graphs of values retrieved from more than one sensor of the measurement device.

12. The method of claim 8, further comprising:
detecting, by the mobile computing device, a warning status presented by a measurement device; and
displaying, by the mobile computing device, an icon to a user corresponding to the detected warning status.

13. The method of claim 8, further comprising storing metadata associated with one or more stored measurements.

14. The method of claim 13, wherein the metadata includes one or more of a name, a location, and operational parameters.

15. A computer-readable medium having computer-executable instructions stored thereon for evaluating measurement data of an installation of a device under test (DUT) with measurement data of an installation of equipment that is different than the DUT but of a same equipment type as the DUT, wherein in response to execution by one or more processors of a mobile computing device, the computer-executable instructions cause the mobile computing device to:
receive, by the mobile computing device, a first time series of measurements of a first parameter of the DUT obtained by a first measurement device at a first time, and a second time series of measurements of a second parameter of an installation of other equipment of the same equipment type as the DUT obtained by a second measurement device at a second time that is different than the first time;
store, by the mobile computing device, the first and second time series of measurements in a measurement data store accessible by the mobile computing device; and
present a graph of the first and second time series of measurements to a user,
wherein presenting the graph of the first and second time series of measurements to a user includes retrieving measurement data and concurrently presenting the measurement data in the graph showing a comparison of measurement data obtained over time from measurement of the DUT and from measurement of the other equipment of the same equipment type as the DUT.

16. The computer-readable medium of claim 15, wherein the measurement device does not have a measurement data store for storing measurement data.

17. The computer-readable medium of claim 15, wherein the instructions further cause the mobile computing device to present a current measurement as a numeric value side-by-side with the graph of the first and second time series of measurements.

18. The computer-readable medium of claim 15, wherein the instructions further cause the mobile computing device to present separate graphs of values retrieved from more than one sensor of the measurement device.

19. The computer-readable medium of claim 15, wherein the instructions further cause the mobile computing device to:
detect a warning status presented by a measurement device; and
display an icon to a user corresponding to the detected warning status.

20. The computer-readable medium of claim 15, wherein the instructions further cause the mobile computing device to store metadata associated with one or more stored measurements.

21. The computer-readable medium of claim 20, wherein the metadata includes one or more of a name, a location, and operational parameters.

\* \* \* \* \*